United States Patent [19]

Le et al.

[11] Patent Number: 5,134,241
[45] Date of Patent: Jul. 28, 1992

[54] MULTISTAGE OLEFIN UPGRADING PROCESS USING SYNTHETIC MESOPOROUS CRYSTALLINE MATERIAL

[75] Inventors: Quang N. Le, Cherry Hill; Robert T. Thomson, Voorhees; Grant H. Yokomizo, Cherry Hill, all of N.J.

[73] Assignee: Mobil Oil Corporation, Fairfax, Va.

[21] Appl. No.: 718,879

[22] Filed: Jun. 21, 1991

[51] Int. Cl.$^5$ ............................................. C07C 2/00
[52] U.S. Cl. ..................... 585/332; 585/520; 585/530; 585/533; 585/643; 585/648; 585/653; 423/277
[58] Field of Search ............ 585/520, 533, 332

[56] References Cited

U.S. PATENT DOCUMENTS

| | | | |
|---|---|---|---|
| 3,884,835 | 5/1975 | Vaughan | 252/451 |
| 4,091,079 | 5/1978 | Vaughan | 423/328 |
| 4,673,559 | 6/1987 | Derouane et al. | 423/306 |
| 4,791,088 | 12/1988 | Chu et al. | 502/232 |
| 4,849,186 | 7/1989 | Beech et al. | 422/190 |
| 4,880,611 | 11/1989 | von Ballmoos et al. | 423/306 |
| 4,969,987 | 11/1990 | Le et al. | 208/67 |
| 5,057,296 | 10/1991 | Beck | 423/277 |

OTHER PUBLICATIONS

"An X-Ray structural study of cacoxenite, a mineral phosphate", Paul B. Moore Nature, vol. 306, Nov. 24, 1983.

"Low-Temperature Oligomerization of Small Olefins on Zeolite H-ZSM-5. An investigation with High-Resolution Solid-State $^{13}$C-NMR", J. P. van den Berg et al., Journal of Catalysis 80, 130-138 (1983).

"Reaction of Small Olefins on Zeolite H-ZSM-5. A Thermogravimetric Study at Low and Intermediate Temperatures", J. P. van den Berg et al., Journal of Catalysis 80, 139-144 (1983).

Primary Examiner—A. Pal
Assistant Examiner—P. Achutamurthy
Attorney, Agent, or Firm—Alexander J. McKillop; Charles J. Speciale; L. G. Wise

[57] ABSTRACT

A process for upgrading olefinic feedstocks containing lower olefins employing new synthetic catalyst of ultra-large pore crystalline material. The new crystalline material exhibits unusually large sorption capacity demonstrated by its benzene adsorption capacity of greater than about 15 grams benzene/100 grams at 50 torr and 25° C., a hexagonal electron diffraction pattern that can be indexed with a $d_{100}$ value greater than about 18 Angstrom Units and a hexagonal arrangement of uniformly sized pores with a maximum perpendicular cross section of at least about 13 Angstrom units. A multistage process is provided for catalytic oligomerization of lower olefin which comprises contacting olefinic feedstock under catalytic conversion conditions with acid metal-losilicate solid catalyst having the structure of MCM-41 with hexagonal honeycomb lattice structure consisting essentially of uniform pores in the range of about 20 to 100 Angstroms. The oligomerization reaction is very selective, especially when conducted at temperature of about 40° to 250° C., yielding branched intermediate olefins. Low severity reaction permits excellent conversio of lower olefins at pressure of about 100-13,000 pKa range and moderate space velocity. Intermediate oligomers produced over MCM-41, when reacted under cracking/disproportionation conditions yield etherifiable $C_4+$ isoalkenese in good yield.

32 Claims, No Drawings

MULTISTAGE OLEFIN UPGRADING PROCESS USING SYNTHETIC MESOPOROUS CRYSTALLINE MATERIAL

CROSS-REFERENCE TO RELATED APPLICATIONS

This application is related to U.S. patent application Ser. No. 07/625,245 (Vartuli et al) filed Dec. 10, 1990, which is a continuation-in-part of Ser. No. 07/470,008.

FIELD OF THE INVENTION

This invention is directed to selective catalytic conversion of olefinic feedstock employing a catalyst composition comprising synthetic ultra-large pore crystalline material. In particular it relates to two-stage oligomerization and disproportionation of olefins to produce hydrocarbons rich in $C_3$-$C_5$.

BACKGROUND OF THE INVENTION

Recent work in the field of olefin upgrading has resulted in catalytic processes for converting lower olefins to heavier hydrocarbons. Particular interest is shown in a technique wherein gasoline and/or distillate range hydrocarbons can be synthesized over ZSM-5 type medium pore zeolite catalysts at elevated temperature and pressure to provide a product having substantially linear molecular conformations due to the ellipsoidal shape selectivity of certain medium pore catalysts.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. In U.S. Pat. No. 4,227,992 Garwood and Lee disclose the operating conditions for the Mobil Olefin to Gasoline/Distillate (MOGD) process for selective conversion of $C_3+$ olefins to mainly aliphatic hydrocarbons. In a related manner, U.S. Pat. Nos. 4,150,062 and 4,211,640 (Garwood et al) disclose a process for converting olefins to gasoline components.

In the process for catalytic conversion of olefins to heavier hydrocarbons by catalytic oligomerization using a medium pore shape selective acid crystalline zeolite, such as ZSM-5 type catalyst, process conditions can be varied to favor the formation of hydrocarbons of varying molecular weight. At moderate temperature and relatively high pressure, the conversion conditions favor $C_{10}+$ aliphatic product. Lower olefinic feedstocks containing $C_2$-$C_8$ alkenes may be converted; however, the distillate mode conditions of the prior art do not convert a major fraction of ethylene. A typical reactive feedstock consists essentially of $C_3$-$C_6$ mono-olefins, with varying amounts of nonreactive paraffins and the like being acceptable components for ordinary commercial purposes. These prior art oligomerization methods require relatively high temperature to provide adequate conversion, resulting in undesirable cracking reactions and a broad spectrum of carbon numbers in the products. The product of medium pore olefin catalysis can be characterized as nearly linear, with only moderate branching due to the constrained pores of the catylysts.

While low temperature oligomerization is known, prior catalysts have not shown sufficient activity below about 200° C. to be practical in industrial applications. The advantages of low severity oligomerization with medium pore zeolites have been described by Avidan et al in U.S. Pat. No. 4,746,762 and 4,873,385. It is generally understood that low temperature oligomerization can be selective to produce incremental oligomers which have molecular weights as multiples of the monomers, such as isomeric propene oligomers consisting essentially of C6, C9, C12, etc. These reactions are selective without significant cracking of the desired product; however, the relative inactivity of prior art catalysts has prevented development of low temperature processes.

It is an object of this invention to provide an improved process for selective catalytic oligomerization of an olefinic feedstock which comprises contacting said feedstock under low severity catalytic conversion conditions with a novel acid solid catalyst having ultra-large pores and exceptionally high oligomerization activity at low temperature. The resulting oligomers are highly branched, incremental oligomers, which can be further converted under disproportionation or cracking conditions to yield lower olefins rich in tertiary compounds.

A new catalyst material has been found to have excellent oligomerization properties, especially at low reaction temperature.

SUMMARY OF THE INVENTION

The present invention provides a process for catalytic upgrading of lower olefins, such as propene and butenes, wherein a lower olefin feedstock is converted catalytically to a mixture of linear olefins and iso-olefins. The improvement comprises two stages of catalysis including the sequential steps of:

oligomerizing the lower olefin feedstock in a first catalytic stage under low severity oligomerization conditions in contact with a selective acid mesoporous oligomerization catalyst intermediate to produce predominantly highly branched oligomers, such as dimers, trimers, tetramers and higher olefins; and disproportionating at least a portion of intermediate olefins in a separate second catalytic stage under selective olefin cracking conditions in contact with a medium pore acid cracking catalyst to provide enhanced yield of tertiary olefins.

DESCRIPTION OF SPECIFIC EMBODIMENTS

The present invention is particularly useful for upgrading $C_3$-$C_5$ lower olefins in a primary reaction stage to heavier intermediate olefins, such as highly branched $C_6$-$C_{18}+$ hydrocarbons. Numerous mono-olefins, including propene, n-butenes, isobutene, pentenes, mixtures thereof, etc., can be reacted selectively in aliphatic hydrocarbon feedstocks. An advantage of the present process is reaction selectivity, such that non-olefinic products can be avoided as reaction by-products, due to the substantial absence of dehydrogenation, cyclization and alkane formation. However, the feedstocks may contain non-deleterious amounts of paraffins, naphthenes, aromatics.

Reaction temperature for oligomerization may vary widely. Below 40° C. the reaction may be too slow and above 250° C. selectivity may be lost for some products. The preferred range is about 40° to 250° C., especially 80° to 200° C. Pressure can also vary greatly from subatmospheric to very high pressures (e.g.—10 -20,000 kPa, with many process reactions taking place in the 100-13,000 pKa range. By contrast with medium pore zeolites, it has been found that increasing pressure for a given feedstock does not result in higher molecular weight products. This is unexpected behavior for one skilled in the art of zeolitic catalysis. For instance, in propylene oligomerization the distribution of higher incremental oligomers falls dramatically above about 5000 kPa (700 psig) with increased selectivity to hexene and nonene isomers. The reaction may be conducted in the gas phase, liquid phase or dense phase.

Industrial application of the primary stage will ordinarily require at least 50% conversion of feedstock, preferably about 80–100%, and such conversion can be obtained with continuous reactor operation using fixed bed, fluidized bed, moving bed, slurry reactor, etc. Typical space velocities, based on active catalyst are in the range of about 0.1–5/hr WHSV, preferably 0.5–2.

This invention also provides a secondary process step for converting intermediate olefins, e.g., $C_6$–$C_{18}$ monoalkene oligomers. Interstage separation may be used to recover unreacted lower aliphatics as byproduct or recycle, or the second reaction stage may employ unfractionated primary stage effluent as a cascade feedstream for disproportionation/cracking reactions in contact with a shape selective porous zeolite catalyst to provide lower olefins and isoalkene hydrocarbon products, especially propene, n-butenes and $C_4$–$C_5$ tertiary alkenes.

In view of phasing out of leaded gasoline and restrictions on the aromatics content of gasoline fuels, there is a great impetus for developing processes which upgrade olefins to high octane components. One such class of materials is aliphatic tertiary ethers, such as methyl tert-butyl ether (MTBE) and tert-amyl methyl ether (TAME). However, the availability of isobutylene and isoamylene feedstock for these ethers is limited. Therefore, processes for making these olefins from readily available feedstocks are sought. The process described herein is one such process and involves the conversion of readily available refinery feedstock, such as C3 mixed aliphatics from FCC operations, to products rich in lower olefins, such as isobutylene and isoamylene.

The ability of shape selective medium pore zeolites such as ZSM-5 to convert various olefins to tertiary compounds, such as isobutene and isopentenes has been recognized previously (see Garwood et al, European Patent Application 0 026 041; Harandi, U.S. Pat. No. 4,886,925). Zeolitic materials, both natural and synthetic, have been demonstrated in the past to have catalytic properties for various types of hydrocarbon conversion. Recent developments in zeolite catalysts and hydrocarbon conversion processes have created interest in utilizing olefinic feedstocks, such as petroleum refinery streams rich in lower olefins, for the production of $C_4^+$ tertiary olefins.

It has been found that a new zeolite, designated MCM-22, is an effective catalyst for converting oligomeric olefins to isoalkenes at high selectivity. MCM-22 olefin interconversion catalysis is characterized by low yields of undesirable normal C3–C5 alkanes and substantially increased yields of isobutene and isoamylenes, which can be further upgraded to high octane fuel components by conventional etherification.

Oligomerization Catalyst Synthesis and Composition

Recent developments in catalyst technology have provided a group of mesoporous siliceous materials having novel pore geometry. These materials are characterized by substantially uniform hexagonal honeycomb microstructure, with uniform pores having a cell diameter greater than 13 Angstrom units, (preferably in the mesoporous range of about 20–100A). Most prominent among these ultra-large pore size materials is a new metallosilicate called MCM-41, which is usually synthesized with Bronsted acid active sites by incorporating a tetrahedrally coordinated trivalent element, such as Al, Ga, B, or Fe, within the silicate framework. Aluminosilicate materials of this type are thermally and chemically stable, properties favored for acid catalysis; however, the advantages of mesoporous structures may be utilized by employing highly siliceous materials or crystalline metallosilicate having one or more tetrahedral species having varying degrees of acidity. In addition to the preferred aluminosilicates, the gallosilicate, ferrosilicate and borosilicate materials may be employed. Although matrices may be formed with the germanium analog of silicon, these are expensive and generally no better than the metallosilicates.

MCM-41 crystalline structure is readily recognized by its spectrographic characteristics, such as electron micrograph, X-ray diffraction pattern, absorbtion properties, etc., as described in U.S. patent application Ser. No. 07/625,245 (Vartuli et al.).

The catalysts preferred for use herein include the ultra-large pore crystalline aluminosilicates having a silica-to-alumina ratio of about 5:1 to 1000:1 and significant Bronsted acid activity. Acid activity may be measured by acid cracking activity or ammonia absorption properties, such as temperature programmed desorption.

In discussing tetrahedrally coordinated metal oxides of the zeolitic type, it is understood that adjacent metal sites in the matrix are linked by oxygen (i.e., —Si—O—Si—). The honeycomb microstructure of MCM-41 and related mesoporous materials may include several moieties interconnected in a three diminsional matrix or lattice having large hexagonal channels therein forming the ultralarge pores of the catalyst. The repeating units forming the large ring structure of the lattice vary with pore size. A typical catalyst component having Bronsted acid sites consists essentially of crystalline aluminosilicate having the structure of MCM-41, optionally containing 5 to 95 wt. % silica, clay and/or alumina binder. These siliceous materials may be employed in their acid form, ion-exchanged or impregnated with one or more suitable metals, such as Ga, Pd, Zn, Ni, Co and/or other metals of Periodic Groups IIIA to VIIIA and IB to IIB (IUPAC). In the description of preferred embodiments catalyst particles consist essentially of pelletized H-MCM-41 (hydrogen form) catalyst.

The inorganic, non-layered mesoporous crystalline catalytic material employed in this invention has the following composition: $M_{n/q}(W_aX_bY_cZ_dO_h)$; wherein W is a divalent element, such as a divalent first row transition metal, e.g. manganese, cobalt and iron, and/or magnesium, preferably cobalt; X is a trivalent element, such as aluminum, boron, iron and/or gallium, preferably aluminum; Y is a tetravalent element such as silicon and/or germanium, preferably silicon; Z is a pentavalent element, such as phosphorus; M is one or more ions, such as, for example, ammonium, Group IA, IIA and VIIB ions, usually hydrogen, sodium and/or fluoride ions; n is the charge of the composition excluding M expressed as oxides; q is the weighted molar average valence of M; n/q is the number of moles or mole fraction of M; a, b, c, and d are mole fractions of W, X, Y and Z, respectively; h is a number of from 1 to 2.5; and $(a+b+c+d)=1$.

A preferred embodiment of the above crystalline material is when $(a+b+c)$ is greater than d, and $h=2$. A further embodiment is when a and $d=0$, and $h=2$.

In the as-synthesized form, the material of this invention has a composition, on an anhydrous basis, expressed empirically as follows: $rRMM_{n/q}(W_z X_b Y_c Z_d O_h)$: wherein R is the total organic material not included in M as an ion, and r is the coefficient for R, i.e. the number of moles or mole fraction of R.

The M and R components are associated with the material as a result of their presence during crystallization, and are easily removed or, in the case of M, replaced by post-crystallization methods hereinafter more particularly described. To the extent desired, the original M, e.g. sodium or chloride, ions of the as-synthesized material of this invention can be replaced in accordance with techniques well known in the art, at least in part, by ion exchange with other ions. Preferred replacing ions include metal ions, hydrogen ions, hydrogen precursor, e.g. ammonium, ions and mixtures thereof. Particularly preferred ions are those which tailor the catalytic activity for certain hydrocarbon conversion reactions. These include hydrogen, rare earth metals and metals of Groups IA (e.g. K), IIA (e.g. Ca), VIIA (e.g. Mn), VIIIA (e.g. Ni),IB (e.g. Cu), IIB (e.g. Zn), IIIB (e.g. In), IVB (e.g. Sn), and VIIB (e.g. F) of the IUPAC Periodic Table of the Elements.

The crystalline (i.e. meant here as having sufficient order to provide a diffraction pattern such as, for example, by X-ray, electron or neutron diffraction, following calcination with at least one peak) mesoporous material of this invention may be characterized by its heretofore unknown structure, including extremely large pore windows, and high sorption capacity. The term "mesoporous" is used here to indicate crystals having uniform pores within the range of from about 13 Angstroms to about 200 Angstroms. The materials of this invention will have uniform pores within the range of from about 13 Angstroms to about 200 Angstroms, more usually from about 15 Angstroms to about 100 Angstroms. For the purposes of this application, a working definition of "porous" is a material that adsorbs at least 1 gram of a small molecule, such as Ar, $N_2$, n-hexane or cyclohexane, per 100 grams of the solid.

The material of the present invention can be distinguished from other porous inorganic solids by the regularity of its large open pores, whose pore size more nearly resembles that of amorphous or paracrystalline materials, but whose regular arrangement and uniformity of size (pore size distribution within a single phase of, for example, $\pm 25\%$, usually $\pm 15\%$ or less of the average pore size of that phase) resemble more those of crystalline framework materials such as zeolites. The material appears to have a hexagonal arrangement of large open channels that can be synthesized with open internal diameters from about 13 Angstroms to about 200 Angstroms. The term "hexagonal" is intended to encompass not only materials that exhibit mathematically perfect hexagonal symmetry within the limits of experimental measurement, but also those with significant observable deviations from that ideal state. A working definition as applied to the microstructure of the present invention would be that most channels in the material would be surrounded by six nearest neighbor channels at roughly the same distance. Defects and imperfections will cause significant numbers of channels to violate this criterion to varying degrees, depending on the quality of the material's preparation. Samples which exhibit as much as $\pm 25\%$ random deviation from the average repeat distance between adjacent channels still clearly give recognizable images of the present ultra-large pore materials. Comparable variations are also observed in the d100 values from the electron diffraction patterns.

The most regular preparations of the material of the present invention give an X-ray diffraction pattern with a few distinct maxima in the extreme low angle region. The positions of these peaks approximately fit the positions of the hkO reflections from a hexagonal lattice. The X-ray diffraction pattern, however, is not always a sufficient indicator of the presence of these materials, as the degree of regularity in the microstructure and the extent of repetition of the structure within individual particles affect the number of peaks that will be observed. Indeed, preparations with only one distinct peak in the low angle region of the X-ray diffraction pattern have been found to contain substantial amounts of the material in them. Other techniques to illustrate the microstructure of this material are transmission electron microscopy and electron diffraction. Properly oriented specimens of the material show a hexagonal arrangement of large channels and the corresponding electron diffraction pattern gives an approximately hexagonal arrangement of diffraction maxima. The $d_{100}$ spacing of the electron diffraction patterns is the distance between adjacent spots on the hkO projection of the hexagonal lattice and is related to the repeat distance $a_0$ between channels observed in the electron micrographs through the formula $d_{100}=a_0 \sqrt{3}/2$. This $d_{100}$ spacing observed in the electron diffraction patterns corresponds to the d-spacing of a low angle peak in the X-ray diffraction pattern of the material. The most highly ordered preparations of the material obtained so far have 20–40 distinct spots observable in the electron diffraction patterns. These patterns can be indexed with the hexagonal hkO subset of unique reflections of 100, 110, 200, 210, etc., and their symmetry-related reflections.

In its calcined form, the crystalline material of the invention may be further characterized by an X-ray diffraction pattern with at least one peak at a position greater than about 18 Angstrom Units d-spacing (4.909 degrees two-theta for Cu K-alpha radiation) which corresponds to the $d_{100}$ value of the electron diffraction pattern of the material, and an equilibrium benzene adsorption capacity of greater than about 15 grams benzene/100 grams crystal at 50 torr and 25° C. (basis: crystal material having been treated in an attempt to insure no pore blockage by incidental contaminants, if necessary).

The equilibrium benzene adsorption capacity characteristic of this material is measured on the basis of no pore blockage by incidental contaminants. For instance, the sorption test will be conducted on the crystalline material phase having any pore blockage contaminants and water removed by ordinary methods. Water may be removed by dehydration techniques, e.g. thermal treatment. Pore blocking inorganic amorphous materials, e.g. silica, and organics may be removed by contact with acid or base or other chemical agents such that the detrital material will be removed without detrimental effect on the crystal of the invention.

More particularly, the calcined crystalline non-layered material of the invention may be characterized by an X-ray diffraction pattern with at least two peaks at positions greater than about 10 Angstrom Units d-spacing (8.842 degrees two-theta for Cu K-alpha radiation), at least one of which is at a position greater than about 18 Angstrom Units d-spacing, and no peaks at positions less than about 10 Angstrom units d-spacing with relative intensity greater than about 20% of the strongest peak. Still more particularly, the X-ray diffraction pattern of the calcined material of this invention will have no peaks at positions less than about 10 Angstrom units d-spacing with relative intensity greater than about 10% of the strongest peak. In any event, at least one peak in the X-ray diffraction pattern will have a d-spacing that corresponds to the $d_{100}$ value of the electron diffraction pattern of the material.

Still more particularly, the calcined inorganic, non-layered crystalline material of the invention is characterized as having a pore size of about 13 Angstroms or greater as measured by physisorption measurements, hereinafter more particularly set forth. Pore size is considered a maximum perpendicular cross-section pore dimension of the crystal.

X-ray diffraction data were collected on a Scintag PAD X automated diffraction system employing theta-theta geometry, Cu K-alpha radiation, and an energy dispersive X-ray detector. Use of the energy dispersive X-ray detector eliminated the need for incident or diffracted beam monochromators. Both the incident and diffracted X-ray beams were collimated by double slit incident and diffracted collimation systems. The slit sizes used, starting from the X-ray tube source, were 0.5, 1.0, 0.3 and 0.2 mm, respectively. Different slit systems may produce differing intensities for the peaks. The materials of the present invention that have the largest pore sizes may require more highly collimated incident X-ray beams in order to resolve the low angle peak from the transmitted incident X-ray beam.

The diffraction data were recorded by step-scanning at 0.04 degrees of two-theta, where theta is the Bragg angle, and a counting time of 10 seconds for each step. The interplanar spacings, d's, were calculated in Angstrom units (A), and the relative intensities of the lines, $I/I_o$, where $I_o$ is one-hundredth of the intensity of the strongest line, above background, were derived with the use of a profile fitting routine. The intensities were uncorrected for Lorentz and polarization effects. The relative intensities are given in terms of the symbols vs=very strong (75-100), s=strong (50-74), m=medium (25-49) and w=weak (0-24). It should be understood that diffraction data listed as single lines may consist of multiple overlapping lines which under certain conditions, such as very high experimental resolution or crystallographic changes, may appear as resolved or partially resolved lines. Typically, crystallographic changes can include minor changes in unit cell parameters and/or a change in crystal symmetry, without a substantial change in structure. These minor effects, including changes in relative intensities, can also occur as a result of differences in cation content, framework composition, nature and degree of pore filling, thermal and/or hydrothermal history, and peak width/shape variations due to particle size/shape effects, structural disorder or other factors known to those skilled in the art of X-ray diffraction.

The equilibrium benzene adsorption capacity is determined by contacting the material of the invention, after dehydration or calcination at, for example, about 540° C. for at least about one hour and other treatment, if necessary, in an attempt to remove any pore blocking contaminants, at 25° C. and 50 torr benzene until equilibrium is reached. The weight of benzene sorbed is then determined as more particularly described hereinafter.

When used as a sorbent or catalyst component, the composition of the invention should be subjected to treatment to remove part or all of any organic constituent. The present composition can also be used as a catalyst component in intimate combination with a hydrogenating component such as tungsten, vanadium, molybdenum, rhenium, nickel, cobalt, chromium, manganese, or a noble metal such as platinum or palladium or mixtures thereof where a hydrogenation-dehydrogenation function is to be performed. Such component can be in the composition by way of co-crystallization, exchanged into the composition to the extent a Group IIIB element, e.g. aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above crystalline material, especially in its metal, hydrogen and ammonium forms can be beneficially converted to another form by thermal treatment (calcination). This thermal treatment is generally performed by heating one of these forms at a temperature of at least 400° C. for at least 1 minute and generally not longer than 20 hours, preferably from about 1 to about 10 hours. While subatmospheric pressure can be employed for the thermal treatment, atmospheric pressure is desired for reasons of convenience, such as in air, nitrogen, ammonia, etc. The thermal treatment can be performed at a temperature up to about 750° C. The thermally treated product is particularly useful in the catalysis of certain hydrocarbon conversion reactions.

The crystalline material of this invention, when employed either as an adsorbent or as a catalyst component in an organic compound conversion process should be dehydrated, at least partially. This can be done by heating to a temperature in the range of 200° C. to 595° C. in an atmosphere such as air, nitrogen, etc. and at atmospheric, subatmospheric or superatmospheric pressures for between 30 minutes and 48 hours. Dehydration can also be performed at room temperature merely by placing the composition in a vacuum, but a longer time is required to obtain a sufficient amount of dehydration.

The present crystalline material can be prepared by one of several methods, each with particular limitations.

A first method involves a reaction mixture having an $X_2O_3/YO_2$ mole ratio of from 0 to about 0.5, but an $Al_2O_3/SiO_2$ mole ratio of from 0 to 0.01, a crystallization temperature of from about 25° C. to about 250° C., preferably from about 50° C. to about 175° C., and an organic directing agent, hereinafter more particularly described, or, preferably a combination of that organic directing agent plus an additional organic directing agent, hereinafter more particularly described. This first method comprises preparing a reaction mixture containing sources of, for example, alkali or alkaline earth metal (M), e.g. sodium or potassium, cation if desired, one or a combination of oxides selected from the group consisting of divalent element W, e.g. cobalt, trivalent element X, e.g. aluminum, tetravalent element Y, e.g. silicon, and pentavalent element Z, e.g. phosphorus, an organic (R) directing agent, hereinafter more particularly described, and a solvent or solvent mixture, such as, for example, $C_1-C_6$ alcohols, $C_1-C_6$ diols and/or water, especially water, said reaction mixture having a composition, in terms of mole ratios of oxides, within the following ranges:

| Reactants | Useful | Preferred |
|---|---|---|
| $X_2O_3/YO_2$ | 0 to 0.5 | 0.001 to 0.5 |
| $Al_2O_3/SiO_2$ | 0 to 0.01 | 0.001 to 0.01 |
| $X_2O_3/(YO_2 + Z_2O_5)$ | 0.1 to 100 | 0.1 to 20 |
| $X_2O_3/(YO_2 + WO + Z_2O_5)$ | 0.1 to 100 | 0.1 to 20 |
| Solvent/$(YO_2 + WO + Z_2O_5 + X_2O_3)$ | 1 to 1500 | 5 to 1000 |
| $OH^-/YO_2$ | 0 to 10 | 0 to 5 |
| $(M_{2/e}O + R_{2/f}O)/(YO_2 + WO + Z_2O_5 + X_2O_3)$ | 0.01 to 20 | 0.05 to 5 |
| $M_{2/e}O/(YO_2 + WO + Z_2O_5 + X_2O_3)$ | 0 to 10 | 0 to 5 |
| $R_{2/f}O/(YO_2 + WO + Z_2O_5 + X_2O_3)$ | 0.01 to 2.0 | 0.03 to 1.0 | wherein e and f are the weighted average valences of M and R, respectively.

In this first method, when no Z and/or W oxides are added to the reaction mixture, the pH is important and must be maintained at from about 9 to about 14. When Z and/or W oxides are present in the reaction mixture, the pH is not narrowly important for synthesis of the present crystalline material. In this, as well as the following methods for synthesis of the present material the $R_{2/f}O/(YO_2+WO+Z_2O_5+X_2O_3)$ ratio is important. When this ratio is less than 0.01 or greater than 2.0, impurity products tend to be synthesized at the expense of the present material.

A second method for synthesis of the present crystalline material involves a reaction mixture having an $X_2O_3/YO_2$ mole ratio of from about 0 to about 0.5, a crystallization temperature of from about 25° C. to about 250° C., preferably from about 50° C. to about 175° C., and two separate organic directing agents, i.e. the organic and additional organic directing agents, hereinafter more particularly described. This second method comprises preparing a reaction mixture containing sources of, for example, alkali or alkaline earth metal (M), e.g. sodium or potassium, cation if desired, one or a combination of oxides selected from the group consisting of divalent element W, e.g. cobalt, trivalent element X, e.g. aluminum, tetravalent element Y, e.g. silicon, and pentavalent element Z, e.g. phosphorus, a combination of organic directing agent and additional organic directing agent (R), each hereinafter more particularly described, and a solvent or solvent mixture, such as, for example, $C_1-C_6$ alcohols, $C_1-C_6$ diols and/or water, especially water, said reaction mixture having a composition, in terms of mole ratios of oxides, within the following ranges:

| Reactants | Useful | Preferred |
|---|---|---|
| $X_2O_3/YO_2$ | 0 to 0.5 | 0.001 to 0.5 |
| $X_2O_3/(YO_2 + Z_2O_5)$ | 0.1 to 100 | 0.1 to 20 |
| $X_2O_3/(YO_2 + WO + Z_2O_5)$ | 0.1 to 100 | 0.1 to 20 |
| Solvent/$(YO_2 + WO + Z_2O_5 + X_2O_3)$ | 1 to 1500 | 5 to 1000 |
| $OH^-/YO_2$ | 0 to 10 | 0 to 5 |
| $(M_{2/e}O + R_{2/f}O)/(YO_2 + WO + Z_2O_5 + X_2O_3)$ | 0.01 to 20 | 0.05 to 5 |
| $M_{2/e}O/(YO_2 + WO + Z_2O_5 + X_2O_3)$ | 0 to 10 | 0 to 5 |
| $R_{2/f}O/(YO_2 + WO + Z_2O_5 + X_2O_3)$ | 0.01 to 2.0 | 0.12 to 1.0 | wherein e and f are the weighted average valences of M and R, respectively.

In this second method, when no Z and/or W oxides are added to the reaction mixture, the pH is important and must be maintained at from about 9 to about 14. When Z and/or W oxides are present in the reaction mixture, the pH is not narrowly important for crystallization of the present invention.

A third method for synthesis of the present crystalline material is where X comprises aluminum and Y comprises silicon, the crystallization temperature must be from about 25° C. to about 175° C., preferably from about 50° C. to about 150° C., and an organic directing agent, hereinafter more particularly described, or, preferably a combination of that organic directing agent plus an additional organic agent, hereinafter more particularly described, is used. This third method comprises preparing a reaction mixture containing sources of, for example, alkali or alkaline earth metal (M), e.g. sodium or potassium, cation if desired, one or more sources of aluminum and/or silicon, an organic (R) directing agent, hereinafter more particularly described, and a solvent or solvent mixture, such as, for example $C_1-C_6$ alcohols, $C_1-C_6$ diols and/or water, especially water, said reaction mixture having a composition, in terms of mole ratios of oxides, within the following ranges:

| Reactants | Useful | Preferred |
|---|---|---|
| $Al_2O_3/SiO_2$ | 0 to 0.5 | 0.001 to 0.5 |
| Solvent/$SiO_2$ | 1 to 1500 | 5 to 1000 |
| $OH^-/SiO_2$ | 0 to 10 | 0 to 5 |
| $(M_{2/e}O + R_{2/f}O)/(SiO_2 + Al_2O_3)$ | 0.01 to 20 | 0.05 to 5 |
| $M_{2/e}O/(SiO_2 + Al_2O_3)$ | 0 to 5 | 0 to 3 |
| $R_{2/f}O/(SiO_2 + Al_2O_3)$ | 0.01 to 2 | 0.03 to 1 | wherein e and f are the weighted average valences of M and R, respectively.

In this third method, the pH is important and must be maintained at from about 9 to about 14. This method involves the following steps:

(1) Mix the organic (R) directing agent with the solvent or solvent mixture such that the mole ratio of solvent/$R_{2/f}O$ is within the range of from about 50 to about 800, preferably from about 50 to 500. This mixture constitutes the "primary template" for the synthesis method.

(2) To the primary template mixture of step (1) add the sources of oxides, e.g. silica and/or alumina such that the ratio of $R_{2/f}O/(SiO_2+Al_2O_3)$ is within the range of from about 0.01 to about 2.0.

(3) Agitate the mixture resulting from step (2) at a temperature of from about 20° C. to about 40° C., preferably for from about 5 minutes to about 3 hours.

(4) Allow the mixture to stand with or without agitation, preferably at a temperature of from about 20° C. to about 100° C., and preferably for from about 10 minutes to about 24 hours.

(5) Crystallize the product from step (4) at a temperature of from about 50° C. to about 175° C., preferably for from about 1 hour to about 72 hours. Crystallization temperatures higher in the given ranges are most preferred.

A fourth method for the present synthesis involves the reaction mixture used for the third method, but the following specific procedure with tetraethylorthosilicate the source of silicon oxide:

(1) Mix the organic (R) directing agent with the solvent or solvent mixture such that the mole ratio of solvent/$R_2/O$ is within the range of from about 50 to about 800, preferably from about 50 to 500. This mixture constitutes the "primary template" for the synthesis method.

(2) Mix the primary template mixture of step (1) with tetraethylorthosilicate and a source of aluminum oxide, if desired, such that the $R_2/O/SiO_2$ mole ratio is in the range of from about 0.5 to about 2.0.

(3) Agitate the mixture resulting from step (2) for from about 10 minutes to about 6 hours, preferably from about 30 minutes to about 2 hours, at a temperature of from about 0° C. to about 25° C., and a pH of less than 12. This step permits hydrolysis/polymerization to take place and the resultant mixture will appear cloudy.

(4) Crystallize the product from step (3) at a temperature of from about 25° C. to about 150° C., preferably from about 95° C. to about 110° C., for from about 4 to about 72 hours, preferably from about 16 to about 48 hours.

In each of the above methods, batch crystallization of the present crystalline material can be carried out under either static or agitated, e.g. stirred, conditions in a suitable reactor vessel, such as for example, polypropylene jars or teflon lined or stainless steel autoclaves. Crystallization may also be conducted continuously in suitable equipment. The total useful range of temperatures for crystallization is noted above for each method for a time sufficient for crystallization to occur at the temperature used, e.g. from about 5 minutes to about 14 days. Thereafter, the crystals are separated from the liquid and recovered.

When a source of silicon is used in the synthesis method, it is preferred to use at least in part an organic silicate, such as, for example, a quaternary ammonium silicate. Non-limiting examples of such a silicate include tetramethylammonium silicate and tetraethylorthosilicate.

By adjusting conditions of the synthesis reaction for each method, like temperature, pH and time of reaction, etc., within the above limits, embodiments of the present non-layered crystalline material with a desired average pore size may be prepared. In particular, changing the pH, the temperature or the reaction time may promote formation of product crystals with different average pore size.

Non-limiting examples of various combinations of W, X, Y and Z contemplated for the first and second synthesis methods of the present invention include:

| W  | X  | Y  | Z |
|----|----|----|---|
| —  | Al | Si | — |
| —  | Al | —  | P |
| —  | Al | Si | P |
| Co | Al | —  | P |
| Co | Al | Si | P |
| —  | —  | Si | — | including the combinations of W being Mg, or an element selected from the divalent first row transition metals, e.g. Mn, Co and Fe; X being B, Ga or Fe; and Y being Ge.

An organic directing agent for use in each of the above methods for synthesizing the present material from the respective reaction mixtures is an ammonium or phosphonium ion of the formula $R_1R_2R_3R_4Q^+$, i.e.:

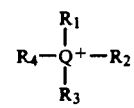

wherein Q is nitrogen or phosphorus and wherein at least one of $R_1$, $R_2$, $R_3$ and $R_4$ is aryl or alkyl of from 6 to about 36 carbon atoms, e.g. $-C_6H_{13}$, $-C_{10}H_{21}$, $-C_{16}H_{33}$ and $-C_{18}H_{37}$, or combinations thereof, the remainder of $R_1$, $R_2$, $R_3$ and $R_4$ being selected from the group consisting of hydrogen, alkyl of from 1 to 5 carbon atoms and combinations thereof. The compound from which the above ammonium or phosphonium ion is derived may be, for example, the hydroxide, halide, silicate, or mixtures thereof.

In the first and third methods above it is preferred to have an additional organic directing agent and in the second method it is required to have a combination of the above organic directing agent and an additional organic directing agent. That additional organic directing agent is the ammonium or phosphonium ion of the above directing agent formula wherein $R_1$, $R_2$, $R_3$ and $R_4$ together or separately are selected from the group consisting of hydrogen and alkyl of 1 to 5 carbon atoms and combinations thereof. Any such combination of organic directing agents go to make up "R" and will be in molar ratio of about 100/1 to about 0.01/1, first above listed organic directing agent/additional organic directing agent.

The particular effectiveness of the presently required directing agent, when compared with other such agents known to direct synthesis of one or more other crystal structures, is believed due to its ability to function as a template in the above reaction mixture in the nucleation and growth of the desired ultra-large pore crystals with the limitations discussed above. Non-limiting examples of these directing agents include cetyltrimethylammonium, cetyltrimethylphosphonium, octadecyltrimethylphosphonium, benzyltrimethylammonium, cetylpyridinium, myristyltrimethylammonium, decyltrimethylammonium, dodecyltrimethylammonium and dimethyldidodecylammonium.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In the examples metric units and parts by weight are employed unless otherwise indicated.

EXAMPLE 1

One hundred grams of cetyltrimethylammonium (CTMA) hydroxide solution, prepared by contacting a 29 wt. % N,N,N-trimethyl-1-hexadecanaminium chloride solution with a hydroxide-for-halide exchange resin, was combined with 100 grams of an aqueous solution of tetramethylammonium (TMA) silicate (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a polypropylene bottle, which was kept in a steam box at 95° C. overnight. The mixture had a composition in terms of moles per mole $Al_2O_3$:

| 2.7 moles | $Na_2O$ |
|---|---|
| 392 moles | $SiO_2$ |
| 35.7 moles | $(CTMA)_2O$ |
| 61.7 moles | $(TMA)_2O$ |
| 6231 moles | $H_2O$ |

The resulting solid product was recovered by filtration and dried in air at ambient temperature. The product was then calcined at 540° C. for 1 hour in nitrogen, followed by 6 hours in air.

The calcined product proved to have a surface area of 475 $m^2/g$ and the following equilibrium adsorption capacities in grams/100 grams:

| $H_2O$ | 8.3 |
|---|---|
| Cyclohexane | 22.9 |
| n-Hexane | 18.2 |
| Benzene | 21.5 |

The product of this example may be characterized as including a very strong relative intensity line at 37.8±2.0 Angstroms d-spacing, and weak lines at 21.6±1.0 and 19.2±1.0 Angstroms. The present ultra-large pore material was demonstrated to be in the product of this example by transmission electron microscopy (TEM), which produced images of a hexagonal arrangement of uniform pores and hexagonal electron diffraction pattern with a $d_{100}$ value of about 39 Angstroms.

EXAMPLE 2

One hundred grams of cetyltrimethylammonium (CTMA) hydroxide solution prepared as in Example 1 was combined with 100 grams of an aqueous solution of tetramethylammonium (TMA) hydroxide (25%) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. overnight. The mixture had a composition in terms of moles per mole $Al_2O_3$:

| 2.7 moles | $Na_2O$ |
|---|---|
| 291 moles | $SiO_2$ |
| 35.7 moles | $(CTMA)_2O$ |
| 102 moles | $(TMA)_2O$ |
| 6120 moles | $H_2O$ |

The resulting solid product was recovered by filtration and dried in air at ambient temperature. The product was then calcined at 540° C. for 1 hour in nitrogen, followed by 6 hours in air.

The calcined product proved to have a surface area of 993 $m^2/g$ and the following equilibrium adsorption capacities in grams/100 grams:

| $H_2O$ | 7.1 |
|---|---|
| Cyclohexane | 47.2 |
| n-Hexane | 36.2 |
| Benzene | 49.5 |

The X-ray diffraction pattern of the calcined product of this example is characterized as including a very strong relative intensity line at 39.3±2.0 Angstroms d-spacing, and weak lines at 22.2±1.0 and 19.4±1.0 Angstroms. TEM indicated that the product contained the present ultra-large pore material.

A portion of the above product was then contacted with steam at 1450° F. for two hours. The surface area of the steamed material was measured to be 440 $m^2/g$, indicating that about 45% was retained following severe steaming.

Another portion of the calcined product of this example was contacted with 100% steam at 1250° F. for two hours. The surface area of this material was measured to be 718 $m^2/g$, indicating that 72% was retained after steaming at these conditions.

EXAMPLE 3

Water, cetyltrimethylammonium hydroxide solution prepared as in Example 1, aluminum sulfate, HiSil and an aqueous solution of tetrapropylammonium (TPA) bromide (35%) were combined to produce a mixture having a composition in terms of moles per mole $Al_2O_3$:

| 0.65 moles | $Na_2O$ |
|---|---|
| 65 moles | $SiO_2$ |
| 8.8 moles | $(CTMA)_2O$ |
| 1.22 moles | $(TPA)_2O$ |
| 1336 moles | $H_2O$ |

The resulting mixture was placed in a polypropylene bottle, which was kept in a steam box at 95° C. for 192 hours. The sample was then cooled to room temperature and combined with CTMA hydroxide solution prepared as in Example 1 and TMA hydroxide (25% by weight) in the weight ratio of 3 parts mixture, 1 part CTMA hydroxide and 2 parts TMA hydroxide. The combined mixture was then placed in a polypropylene bottle and kept in a steam box at 95° C. overnight. The combined mixture had a composition in terms of moles per mole $Al_2O_3$:

| 0.65 moles | $Na_2O$ |
|---|---|
| 65 moles | $SiO_2$ |
| 15 moles | $(CTMA)_2O$ |
| 1.22 moles | $(TPA)_2O$ |
| 35.6 moles | $(TMA)_2O$ |
| 2927 moles | $H_2O$ |

The resulting solid product was recovered by filtration and dried in air at ambient temperature. The product was then calcined at 540° C. for 1 hour in nitrogen, followed by 6 hours in air.

The calcined product proved to have a surface area of 1085 m²/g and the following equilibrium adsorption capacities in grams/100 grams:

| H₂O | 11.5 |
|---|---|
| Cyclohexane | >50 |
| n-Hexane | 39.8 |
| Benzene | 62 |

The X-ray diffraction pattern of the calcined product of this example is characterized as including a very strong relative intensity line at 38.2±2.0 Angstroms d-spacing, and weak lines at 22.2±1.0 and 19.4±1.0 Angstroms. TEM indicated the product contained the present ultra-large pore material.

EXAMPLE 4

Two hundred grams of cetyltrimethylammonium (CTMA) hydroxide solution prepared as in Example 1 was combined with 2 grams of Catapal alumina (alpha-alumina monohydrate, 74% alumina) and 100 grams of an aqueous solution of tetramethylammonium (TMA) silicate (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. for 48 hours. The mixture had a composition in terms of moles per mole $Al_2O_3$:

| 0.23 moles | Na₂O |
|---|---|
| 33.2 moles | SiO₂ |
| 6.1 moles | (CTMA)₂O |
| 5.2 moles | (TMA)₂O |
| 780 moles | H₂O |

The resulting solid product was recovered by filtration and dried in air at ambient temperature. The product was then calcined at 540° C. for 1 hour in nitrogen, followed by 6 hours in air.

The calcined product proved to have a surface area of 1043 m²/g and the following equilibrium adsorption capacities in grams/100 grams:

| H₂O | 6.3 |
|---|---|
| Cyclohexane | >50 |
| n-Hexane | 49.1 |
| Benzene | 66.7 |

The X-ray diffraction pattern of the calcined product of this example is characterized as including a very strong relative intensity line at 40.8±2.0 Angstroms d-spacing, and weak lines at 23.1±1.0 and 20.1±1.0 Angstroms. TEM indicated that the product contained the present ultra-large pore material (see Example 23).

EXAMPLE 5

Two-hundred sixty grams of water was combined with 77 grams of phosphoric acid (85%), 46 grams of Catapal alumina (74% alumina), and 24 grams of pyrrolidine (Pyr) with stirring. This first mixture was placed in a stirred autoclave and heated to 150° C. for six days. The material was filtered, washed and air-dried. Fifty grams of this product was slurried with 200 grams of water and 200 grams of cetyltrimethylammonium hydroxide solution prepared as in Example 1. Four hundred grams of an aqueous solution of tetraethylammonium silicate (10% silica) was then added to form a second mixture which was placed in a polypropylene bottle and kept in a steam box at 95° C. overnight. The first mixture had a composition in terms of moles per mole $Al_2O_3$:

| 1.0 moles | P₂O₅ |
|---|---|
| 0.51 moles | (Pyr)₂O |
| 47.2 moles | H₂O |

The resulting solid product was recovered by filtration and dried in air at ambient temperature. The product was then calcined at 540° C. for 1 hour in nitrogen, followed by 6 hours in air.

The calcined product proved to have a surface area of 707 m²/g and the following equilibrium adsorption capacities in grams/100 grams:

| H₂O | 33.2 |
|---|---|
| Cyclohexane | 19.7 |
| n-Hexane | 20.1 |
| Benzene | 23.3 |

The X-ray diffraction pattern of the calcined product of this example is characterized as including a very strong relative intensity line at 25.4±1.5 Angstroms d-spacing. TEM indicated the product contained the present ultra-large pore material (see Example 23).

EXAMPLE 6

A solution of 1.35 grams of NaAlO₂ (43.5% Al₂O₃, 30% Na₂O) dissolved in 45.2 grams of water was mixed with 17.3 grams of NaOH, 125.3 grams of colloidal silica (40%, Ludox HS-40) and 42.6 grams of 40% aqueous solution of tetraethylammonium (TEA) hydroxide. After stirring overnight, the mixture was heated for 7 days in a steam box (95° C.). Following filtration, 151 grams of this solution was mixed with 31 grams of cetyltrimethylammonium hydroxide solution prepared as in Example 1 and stored in the steam box at 95° C. for 13 days. The mixture had the following relative molar composition:

| 0.25 moles | Al₂O₃ |
|---|---|
| 10 moles | Na₂O |
| 36 moles | SiO₂ |
| 0.95 moles | (CTMA)₂O |
| 2.5 moles | (TEA)₂O |
| 445 moles | H₂O |

The resulting solid product was recovered by filtration and washed with water and ethanol. The product was then calcined at 540° C. for 1 hour in nitrogen, followed by 6 hours in air.

The calcined product composition included 0.14 wt. % Na, 68.5 wt. % SiO₂ and 5.1 wt. % Al₂O₃, and proved to have a benzene equilibrium adsorption capacity of 58.6 grams/100 grams.

The X-ray diffraction pattern of the calcined product of this example is characterized as including a very strong relative intensity line at 31.4±1.5 Angstroms d-spacing. TEM indicated that the product contained the present ultra-large pore material.

EXAMPLE 7

A mixture of 300 grams of cetyltrimethylammonium (CTMA) hydroxide solution prepared as in Example 1 and 41 grams of colloidal silica (40%, Ludox HS-40) was heated in a 600 cc autoclave at 150° C. for 48 hours with stirring at 200 rpm. The mixture has a composition in terms of moles per mole $SiO_2$:

| 0.5 mole | $(CTMA)_2O$ |
| 46.5 moles | $H_2O$ |

The resulting solid product was recovered by filtration, washed with water, then calcined at 540° C. for 1 hour in nitrogen, followed by 10 hours in air.

The calcined product composition included less than 0.01 wt. % Na, about 98.7 wt. % $SiO_2$ and about 0.01 wt. % $Al_2O_3$, and proved to have a surface area of 896 $m^2/g$. The calcined product had the following equilibrium adsorption capacities in grams/100 grams:

| $H_2O$ | 8.4 |
| Cyclohexane | 49.8 |
| n-Hexane | 42.3 |
| Benzene | 55.7 |

The X-ray diffraction pattern of the calcined product of this example is characterized as including a very strong relative intensity line at 40.0±2.0 Angstroms d-spacing and a weak line at 21.2±1.0 Angstroms. TEM indicated that the product of this example contained at least three separate phases, one of which was the present ultra-large pore material.

EXAMPLE 8

A mixture of 150 grams of cetyltrimethylammonium (CTMA) hydroxide solution prepared as in Example 1 and 21 grams of colloidal silica (40%, Ludox HS-40) with an initial pH of 12.64 was heated in a 300 cc autoclave at 150° C. for 48 hours with stirring at 200 rpm. The mixture had a composition in terms of moles per mole $SiO_2$:

| 0.5 mole | $(CTMA)_2O$ |
| 46.5 moles | $H_2O$ |

The resulting solid product was recovered by filtration, washed with water, then calcined at 540° C. for 6 hours in air.

The calcined product composition was measured to include 0.01 wt. % Na, 93.2 wt. % $SiO_2$ and 0.016 wt. % $Al_2O_3$, and proved to have a surface area of 992 $m^2/g$ and the following equilibrium adsorption capacities in grams/100 grams:

| $H_2O$ | 4.6 |
| Cyclohexane | >50 |
| n-Hexane | >50 |
| Benzene | 62.7 |

The X-ray diffraction pattern of the calcined product of this example is characterized as including a very strong relative intensity line at 43.6±2.0 Angstroms d-spacing and weak lines at 25.1±1.5 and 21.7±1.0 Angstroms. TEM indicated that the product contained the present ultra-large pore material.

EXAMPLE 9

Sodium aluminate (4.15 g) was added slowly into a solution containing 16 g of myristyltrimethylammonium bromide ($C_{14}$TMABr) in 100 g of water. Tetramethylammonium silicate (100 g-10% $SiO_2$), HiSil (25 g) and tetramethylammonium hydroxide (14.2 g-25% solution) were then added to the mixture. The mixture was crystallized in an autoclave at 120° C. with stirring for 24 hours.

The product was filtered, washed and air dried. Elemental analysis showed the product contained 53.3 wt. % $SiO_2$, 3.2 wt. % $Al_2O_3$, 15.0 wt. % C, 1.88 wt. % N, 0.11 wt. % Na and 53.5 wt. % ash at 1000° C. The X-ray diffraction pattern of the material (calcined at 540° C. for 1 hour in $N_2$ and 6 hours in air) includes a very strong relative intensity line at 35.3±2.0 Angstroms d-spacing and weak lines at 20.4±1.0 and 17.7±1.0 Angstroms d-spacing. TEM indicated that the product contained the present ultra-large pore material.

The washed product, having been exchanged with 1N ammonium nitrate solution at room temperature, then calcined, proved to have a surface area of 827 $m^2/g$ and the following equilibrium adsorption capacities in g/100 g anhydrous sorbent:

| $H_2O$ | 30.8 |
| Cyclohexane | 33.0 |
| n-Hexane | 27.9 |
| Benzene | 40.7 |

EXAMPLE 10

Sodium aluminate (4.15 g) was added slowly into a solution containing 480 g of dodecyltrimethylammonium hydroxide $C_{12}$TMAOH, 50%) solution diluted with 120 g of water. UltraSil (50 g) and an aqueous solution of tetramethylammonium silicate (200 g-10% $SiO_2$) and tetramethylammonium hydroxide (26.38 g-25% solution) were then added to the mixture. The mixture was crystallized in an autoclave at 100° C. with stirring for 24 hours. The product was filtered, washed and air dried. The X-ray diffraction pattern of the material (calcined at 540° C. for 1 hour in $N_2$ and 6 hours in air) includes a very strong relative intensity line at 30.4±1.5 Angstroms d-spacing and weak lines at 17.7±1.0 and 15.3±1.0 Angstroms d-spacing. TEM indicated that the product contained the present ultra-large pore material.

The washed product, having been exchanged with 1N ammonium nitrate solution at room temperature, then calcined, proved to have a surface area of 1078 $m^2/g$ and the following equilibrium adsorption capacities in g/100 g anhydrous sorbent:

| $H_2O$ | 32.6 |
| Cyclohexane | 38.1 |
| n-Hexane | 33.3 |
| Benzene | 42.9 |

EXAMPLE 11

A solution of 4.9 grams of $NaAlO_2$ (43.5 % $Al_2O_3$, 30% $NaO_2$) in 37.5 grams of water was mixed with 46.3 cc of 40% aqueous tetraethylammonium hydroxide solution and 96 grams of colloidal silica (40%, Ludox HS-40). The gel was stirred vigorously for 0.5 hour, mixed with an equal volume (150 ml) of cetyltrimethylammonium hydroxide solution prepared as in Example 1 and reacted at 100° C. for 168 hours. The mixture had the following composition in terms of moles per mole $Al_2O_3$:

| | |
|---|---|
| 1.1 moles | $Na_2O$ |
| 30.6 moles | $SiO_2$ |
| 3.0 moles | $(TEA)_2O$ |
| 3.25 moles | $(CTMA)_2O$ |
| 609 moles | $H_2O$ |

The resulting solid product was recovered by filtration, washed with water then calcined at 540° C. for 16 hours in air.

The calcined product proved to have a surface area of 1352 $m^2/g$ and the following equilibrium adsorption capacities in grams/100 grams:

| | |
|---|---|
| $H_2O$ | 23.6 |
| Cyclohexane | >50 |
| n-Hexane | 49 |
| Benzene | 67.5 |

The X-ray diffraction pattern of the calcined product of this example may be characterized as including a very strong relative intensity line at 38.5±2.0 Angstroms d-spacing and a weak line at 20.3±1.0 Angstroms. TEM indicated that the product contained the present ultra-large pore material.

EXAMPLE 12

Two hundred grams of cetyltrimethylammonium (CTMA) hydroxide solution prepared as in Example 1 was combined with 4.15 grams of sodium aluminate and 100 grams of aqueous tetramethylammonium (TMA) silicate solution (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. for 24 hours. The mixture had a composition in terms of moles per mole $Al_2O_3$:

| | |
|---|---|
| 1.25 moles | $Na_2O$ |
| 27.8 moles | $SiO_2$ |
| 5.1 moles | $(CTMA)_2O$ |
| 4.40 moles | $(TMA)_2O$ |
| 650 moles | $H_2O$ |

The resulting solid product was recovered by filtration and dried in air at ambient temperature. The product was then calcined at 540° C. for 1 hour in nitrogen, followed by 6 hours in air. TEM indicated that this product contained the present ultra-large pore material. The X-ray diffraction pattern of the calcined product of this example can be characterized as including a very strong relative intensity line at 44.2±2.0 Angstroms d-spacing and weak lines at 25.2±1.5 and 22.0±1.0 Angstroms.

The calcined product proved to have a surface area of 932 $m^2/g$ and the following equilibrium adsorption capacities in grams/100 grams:

| | |
|---|---|
| $H_2O$ | 39.3 |
| Cyclohexane | 46.6 |
| n-Hexane | 37.5 |
| Benzene | 50 |

The product of this example was then ammonium exchanged with 1N $NH_4NO_3$ solution, followed by calcination at 540° C. for 10 hours in air.

EXAMPLE 13

Two hundred grams of cetyltrimethylammonium (CTMA) hydroxide solution prepared as in Example 1 was combined with 4.15 grams of sodium aluminate and 100 grams of aqueous tetramethylammonium (TMA) silicate solution (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a steam box at 100° C. for 48 hours. The mixture had a composition in terms of moles per mole $Al_2O_3$:

| | |
|---|---|
| 1.25 moles | $Na_2O$ |
| 27.8 moles | $SiO_2$ |
| 5.1 moles | $(CTMA)_2O$ |
| 4.4 moles | $(TMA)_2O$ |
| 650 moles | $H_2O$ |

The resulting solid product was recovered by filtration and dried in air at ambient temperature. The product was then calcined at 540° C. for 1 hour in nitrogen, followed by 6 hours in air.

The calcined product proved to have the following equilibrium adsorption capacities in grams/100 grams:

| | |
|---|---|
| $H_2O$ | 35.2 |
| Cyclohexane | >50 |
| n-Hexane | 40.8 |
| Benzene | 53.5 |

The X-ray diffraction pattern of the calcined product of this example may be characterized as including a very strong relative intensity line at 39.1±2.0 Angstroms d-spacing and weak lines at 22.4±1.0 and 19.4±1.0 Angstroms. TEM indicated that this product contained the present ultra-large pore material.

The product of this example was then ammonium exchanged with 1N $NH_4NO_3$ solution, followed by calcination at 540° C. for 10 hours in air.

EXAMPLE 14

A mixture of 125 grams of 29% CTMA chloride aqueous solution, 200 grams of water, 3 grams of sodium aluminate (in 50 grams $H_2O$), 65 grams of Ultrasil, amorphous precipitated silica available from PQ Corporation, and 21 grams NaOH (in 50 grams $H_2O$) was stirred thoroughly and crystallized at 150° C. for 168 hours. The reaction mixture had the following relative molar composition in terms of moles per mole silica:

| | |
|---|---|
| 0.10 moles | $(CTMA)_2O$ |
| 21.89 moles | $H_2O$ |
| 0.036 moles | $NaAlO_2$ |
| 0.53 moles | NaOH |

The solid product was isolated by filtration, washed with water, dried for 16 hours at room temperature and calcined at 540° C. for 10 hours in air.

The calcined product proved to have a surface area of 840 m²/g, and the following equilibrium adsorption capacities in grams/100 grams:

| | |
|---|---|
| H₂O | 15.2 |
| Cyclohexane | 42.0 |
| n-Hexane | 26.5 |
| Benzene | 62 |

The X-ray diffraction pattern of the calcined product of this Example may be characterized as including a very strong relative intensity line at 40.5±2.0 Angstroms d-spacing. TEM indicated that the product contained the present ultra-large pore material.

EXAMPLE 15

For comparison purposes, a commercially prepared ultra-stable zeolite Y was obtained. It had a benzene equilibrium adsorption capacity of 20.7 grams/100 grams. Its X-ray diffraction pattern had all the lines of zeolite Y with its highest value peak at about 14.0 Angstroms d-spacing.

EXAMPLE 16

To make the primary template mixture for this example, 240 grams of water was added to a 92 gram solution of 50% dodecyltrimethylammonium hydroxide, 36% isopropyl alcohol and 14% water such that the mole ratio of Solvent/$R_{2/f}O$ was 155. The mole ratio of $H_2O/R_{2/f}O$ in this mixture was 149 and the IPA/$R_{2/f}O$ mole ratio was 6. the primary template mixture was added 4.15 grams of sodium aluminate, 25 grams of HiSil, 100 grams of aqueous tetramethylammonium silicate solution (10% $SiO_2$) and 13.2 grams of 25% aqueous tetramethylammonium hydroxide solution. The mole ratio of $R_{2/f}O/(SiO_2+Al_2O_3)$ was 0.28 for the mixture.

This mixture was stirred at 25° C. for 1 hour. The resulting mixture was then placed in an autoclave at 100° C. and stirred at 100 rpm for 24 hours. The mixture in the autoclave had the following relative molar composition in terms of moles per mole $SiO_2$:

| | |
|---|---|
| 0.05 mole | Na₂O |
| 0.036 mole | Al₂O₃ |
| 0.18 mole | (C₁₂TMA)₂O |
| 0.12 mole | (TMA)₂O |
| 36.0 moles | H₂O |
| 1.0 mole | IPA |

The resulting solid product was recovered by filtration, washed with water and dried in air at ambient temperature. The product was then calcined at 540° C. for 1 hour in nitrogen, followed by 6 hours in air.

The calcined product proved to have a surface area of 1223 m²/g and the following equilibrium adsorption capacities in grams/100 grams:

| | |
|---|---|
| H₂O | 25.5 |
| Cyclohexane | 41.1 |
| n-Hexane | 35.1 |
| Benzene | 51 |

The X-ray diffraction pattern of the calcined product of this example is characterized as including a very strong relative intensity lnie at 30.8±1.5 Angstroms d-spacing and weak lines at 17.9±1.0 and 15.5±1.0 Angstroms. TEM indicated this product to contain the present ultra-large pore material.

EXAMPLE 17

A 50.75 gram quantity of decyltrimethylammonium hydroxide (prepared by contacting a ca. 29 wt. % solution of decyltrimethylammonium bromide with a hydroxide-for-halide exchange resin) was combined with 8.75 grams of tetraethylorthosilicate. The mixture was stirred for about 1 hour and then transferred to a polypropylene jar which was then placed in a steambox for about 24 hours. The mixture had a composition in terms of moles per mole $SiO_2$:

| | |
|---|---|
| 0.81 mole | (C₁₀TMA)₂O |
| 47.6 moles | H₂O |

The resulting solid product was filtered and washed several times with warm (60°–70° C.) distilled water and with acetone. The final product was calcined to 538° C. in N₂/air mixture and then held in air for about 8 hours.

The calcined product proved to have a surface area of 915 m²/g and an equilibrium benzene adsorption capacity of 35 grams/100 grams. Argon physisorption data indicated an argon uptake of 0.34 cc/gram, and a pore size of 15 Angstroms.

The X-ray diffraction pattern of the calcined product of this example may be characterized as including a very strong relative intensity line at 27.5±1.5 Angstroms d-spacing and weak lines at 15.8±1.0 and 13.7±1.0 Angstroms. TEM indicated that the product of this example contained the present ultra-large pore material.

EXAMPLE 18

To eighty grams of cetyltrimethylammonium hydroxide (CTMAOH) solution prepared as in Example 1 was added 1.65 grams of NaAlO₂. The mixture was stirred at room temperature until the NaAlO₂ was dissolved. To this solution was added 40 grams of aqueous tetramethylammonium (TMA) silicate solution (10 wt. % $SiO_2$), 10 grams of HiSil, 200 grams of water and 70 grams of 1,3,5-trimethylbenzene (mesitylene). The resulting mixture was stirred at room temperature for several minutes. The gel was then loaded into a 600 cc autoclave and heated at 105° C. for sixty-eight hours with stirring at 150 rpm. The mixture had a composition in terms of moles per mole Al₂O₃:

| | |
|---|---|
| 1.25 moles | Na₂O |
| 27.8 moles | SiO₂ |
| 5.1 moles | (CTMA)₂O |
| 2.24 moles | (TMA)₂O |
| 2256 moles | H₂O |
| 80.53 moles | 1,3,5-trimethylbenzene |

The resulting product was filtered and washed several times with warm (60°–70° C.) distilled water and with acetone. The final product was calcined to 538° C. in N₂/air mixture and then held in air for about 10 hours.

The calcined product proved to have an equlibrium benzene adsorption capacity of >25 grams/100 grams.

The X-ray diffraction pattern of the calcined product of this example may be characterized as including a broad, very strong relative intensity line at about 102 Angstroms d-spacing, but accurate positions of lines in the extreme low angle region of the X-ray diffraction pattern are very difficult to determine with conventional X-ray diffractometers. Furthermore, finer collimating slits were required to resolve a peak at this low 2-theta angle. The slits used in this example, starting at the X-ray tube, were 0.1, 0.3, 0.5 and 0.2 mm, respectively. TEM indicated that the product of this example contained several materials with different $d_{100}$ values as observed in their electron diffraction patterns. These materials were found to possess $d_{100}$ values between about 85 Angstroms d-spacing and about 120 Angstroms d-spacing.

EXAMPLE 19

To eighty grams of cetyltrimethylammonium hydroxide (CTMAOH) solution prepared as in Example 1 was added 1.65 grams of NaAlO$_2$. The mixture was stirred at room temperature until the NaAlO$_2$ was dissolved. To this solution was added 40 grams of aqueous tetramethylammonium (TMA) silicate solution (10 wt. % SiO$_2$), 10 grams of HiSil, 200 grams of water and 120 grams of 1,3,5-trimethylbenzene (mesitylene). The resulting mixture was stirred at room temperature for several minutes. The gel was then loaded into a 600 cc autoclave and heated at 105° C. for ninety hours with stirring at 150 rpm. The mixture had a composition in terms of moles per mole Al$_2$O$_3$:

| | |
|---|---|
| 1.25 | moles Na$_2$O |
| 27.8 | moles SiO$_2$ |
| 5.1 | moles (CTMA)$_2$O |
| 2.24 | moles (TMA)$_2$O |
| 2256 | moles H$_2$O |
| 132.7 | moles 1,3,5-trimethylbenzene |

The resulting product was filtered and washed several times with warm (60°-70° C.) distilled water and with acetone. The final product was calcined to 538° C. in N$_2$/air mixture and then held in air for about 10 hours.

The calcined product proved to have a surface area of 915 m$^2$/g and an equilbrium benzene adsorption capacity of >25 grams/100 grams. Argon physisorption data indicated an argon uptake of 0.95 cc/gram, and a pore size centered on 78 Angstroms (Dollimore-Heal Method, see Example 22(b)), but running from 70 to greater than 105 Angstroms.

The X-ray diffraction pattern of the calcined product of this example may be characterized as having only enhanced scattered intensity in the very low angle region of the X-ray diffraction, where intensity from the transmitted incident X-ray beam is usually observed. However, TEM indicated that the product of this example contained several materials with different d100 values as observed in their electron diffraction patterns. These materials were found to possess d100 values between about 85 Angstroms d-spacing and about 110 Angstroms d-spacing.

EXAMPLE 20

To eighty grams of cetyltrimethylammonium hydroxide (CTMAOH) solution prepared as in Example 1 was added 1.65 grams of NaAlO$_2$. The mixture was stirred at room temperature until the NaAlO$_2$ was dissolved. To this solution was added 40 grams of aqueous tetramethylammonium (TMA) silicate solution (10 wt. % SiO$_2$), 10 grams of HiSil, and 18 grams of 1,3,5-trimethylbenzene (mesitylene). The resulting mixture was stirred at room temperature for several minutes. The gel was then loaded into a 300 cc autoclave and heated at 105° C. for four hours with stirring at 150 rpm. The mixture had a composition in terms of moles per mole Al$_2$O$_3$:

| | |
|---|---|
| 1.25 | moles Na$_2$O |
| 27.8 | moles SiO$_2$ |
| 5.1 | moles (CTMA)$_2$O |
| 2.24 | moles (TMA)$_2$O |
| 650 | moles H$_2$O |
| 19.9 | moles 1,3,5-trimethylbenzene |

The resulting product was filtered and washed several times with warm (60°-70° C.) distilled water and with acetone. The final product was calcined to 538° C. in N$_2$/air mixture and then held in air for about 8 hours.

The calcined product proved to have a surface area of 975 m$^2$/g and an equilbrium benzene adsorption capacity of >40 grams/100 grams. Argon physisorption data indicated an argon uptake of 0.97 cc/gram, and a pore size of 63 Angstroms (Dollimore-Heal Method, see Example 22(b)), with the peak occurring at P/P$_o$=0.65.

The X-ray diffraction pattern of the calcined product of this example may be characterized as including a very strong relative intensity line at 63±5 Angstroms d-spacing and weak lines at 36.4±2.0, 31.3±1.5 Angstroms and 23.8±1.0 Angstroms d-spacing. TEM indicated that the product of this example contained the present ultra-large pore material.

EXAMPLE 21

For catalytic evaluation of the present invention, final products from Examples 1 through 15 were evaluated for dealkylation of tri-tert-butylbenzene (TBB) to di-tert butylbenzene. The present evaluation was conducted under one or both of two sets of conditions: (i) at a temperature of 225° C., weight hourly space velocity of 100 hr or (ii) at a temperature of 200° C., weight hourly space velocity of 200 hr$^{-1}$. Pressure was atmospheric. The feed was composed of 6.3/93.7 TTBB/toluene. Conversion was measured at 30 minutes on stream.

The results were as follows:

| Catalyst of Example | Conversion, wt. % | |
|---|---|---|
| | 225° C./100 hr$^{-1}$ | 200° C./200 hr$^{-1}$ |
| 1 | 0 | — |
| 2 | 6.2 | — |
| 3 | 53.9 | — |
| 4 | 10.4 | — |
| 5 | 68.9 | — |
| 6 | 100.0 | — |
| 7 | 93.4 | 66.0 |
| 8 | 5.3 | — |
| 9 | — | 61.2 |
| 10 | — | 58.9 |
| 11 | 86.3 | — |
| 12 | 96.7 | — |
| 13 | 92.8 | — |
| 14 | — | 37.7 |
| 15 | 12.0 | 0 |

EXAMPLE 22(a)

Argon Physisorption For Pore Systems Up to About 60 Angstroms Diameter

To determine the pore diameters of the products of this invention with pores up to about 60 Angstroms in diameter, 0.2 gram samples of the products of Examples 1 through 17 were placed in glass sample tubes and attached to a physisorption apparatus as described in U.S. Pat. No. 4,762,010, which is incorporated herein by reference.

The samples were heated to 300° C. for 3 hours in vacuo to remove adsorbed water. Thereafter, the samples were cooled to 87° K by immersion of the sample tubes in liquid argon. Metered amounts of gaseous argon were then admitted to the samples in stepwise manner as described in U.S. Pat. No. 4,762,010, column 20. From the amount of argon admitted to the samples and the amount of argon left in the gas space above the samples, the amount of argon adsorbed can be calculated. For this calculation, the ideal gas law and the calibrated sample volumes were used. (See also S. J. Gregg et al., *Adsorption, Surface Area and Porosity*, 2nd ed., Academic Press, 1982). It is common to use relative pressures which are obtained by forming the ratio of the equilibrium pressure and the vapor pressure $P_o$ of the adsorbate at the temperature where the isotherm is measured. Sufficiently small amounts of argon were admitted in each step to generate 168 data points in the relative pressure range from 0 to 0.6. At least about 100 points are required to define the isotherm with sufficient detail.

The step (inflection) in the isotherm, in this case (Example 4 product) at about $P/P_o=0.4$, indicates filling of a pore system. The size of the step indicates the amount adsorbed, whereas the position of the step in terms of $P/P_o$ reflects the size of the pores in which the adsorption takes place. Larger pores are filled at higher $P/P_o$. In order to better locate the position of the step in the isotherm, the derivative with respect to log $(P/P_o)$ is formed. There is further provided a physical scale on the axis which converts the position of an adsorption peak in terms of log $(P/P_o)$ to the physical pore diameter in Angstroms. This conversion was obtained by using the following formula:

$$\log(P/P_o) = \frac{K}{d - 0.38}\left[\frac{S^4}{3(L - D/2)^3} - \frac{S^{10}}{9(L - D/2)^9} - \frac{S^4}{3(D/2)^3} + \frac{S^{10}}{9(D/2)^9}\right]$$

wherein d = pore diameter in nanometers, K = 32.17, S = 0.2446, L = d + 0.19, and D = 0.57.

This formula is derived from the method of Horvath and Kawazoe (G. Horvath et al., *J. Chem. Eng. Japan.* 16 (6) (1983)). The constants required for the implementation of this formula were determined from a measured isotherm of ALPO-5 and its known pore size. This method is particularly useful for microporous materials having pores of up to about 60 Angstroms in diameter.

The pore size of the material of Example 4 is 39.6 Angstroms with the peak occurring at log = −0.4 or $P/P_o=0.4$, while the pore size of the material from U.S. Pat. No. 4,880,611 is 12 Angstroms or $P/P_o=0.02$. In the other materials, a peak is observed at $P/P_o=0.015$ which is denoted by an asterisk in FIG. 17. This peak reflects adsorption on the walls of the pores and is not otherwise indicative of the size of the pores of a given material. A value of $P/P_o$ of 0.03 corresponds to 13 Angstroms pore size.

The results of this procedure for the samples from Examples 1 through 17 are tabulated below. The samples from Examples 10, 13 and 16 gave two separate peaks, believed to be the result of two separate ultra-large pore phases in the products.

| Examples | Pore Diameter, Angstroms |
|---|---|
| 1 | 32.2 |
| 2 | 35.4 |
| 3 | 42.5 |
| 4 | 39.6 |
| 5 | 16.9 |
| 6 | 27.3 |
| 7 | 36.6 |
| 8 | 42.6 |
| 9 | 28.3 |
| 10 | 22.8, 30.8 |
| 11 | 36.8 |
| 12 | 36.1 |
| 13 | 35.0, 42.1 |
| 14 | 40.0 |
| 15 | 8.3 |
| 16 | 22.4, 30.4 |
| 17 | 15.0 |

Process Example A—To demonstrate the catalytic oligomerization properties of MCM-41, experiments are performed with C3 aliphatic feedstock in a fixed bed isothermal tubular reactor containing hydrogen form of MCM-41. The temperature is varied from about 80° C. to 160° C. (175° F.–320° F.). The propene partial pressure ranged from about 1800 kPa to 10,400 kPa (250–1500 psig) and the weight hourly space velocity varied between 0.25 and 1.0 (based on active catalyst). Propylene is oligomerized selectively without detectable propane conversion by contact with MCM-41 catalyst prepared according to the method of Example 13, pelletized to form solid particles having a size range of about 14/60 mesh.

The data contained in Table A show that the ultra large pore MCM-41 zeolite exhibits significantly improved activity compared with ZSM-5 and ZSM-23 for propylene oligomerization. MCM-41 also provides significantly higher $C_9$ and $C_{12}$ hydrocarbon yield for propylene oligomerization as shown in Table B.

TABLE A

| Catalyst | psig | Temp. (°C./°F.) | WHSV | % Conv. $C_3=$ |
|---|---|---|---|---|
| ZSM-5 | 500 | 204/400 | 0.4 | 98 |
| ZSM-23 | 500 | 185/365 | 0.25 | 91 |
| MCM-41 | 500 | 96/205 | 1.0 | 84 |
| MCM-41 | 500 | 96/205 | 0.25 | >98 |

TABLE B

| Catalyst | ZSM-23 | MCM-41 |
|---|---|---|
| Propylene Conv., Wt % | 91 | 98 |
| Product Comp., wt % | | |
| $C_6=$ | 59 | 2 |
| $C_9=$ | 20 | 43 |
| $C_{12}=$ | 11 | 34 |
| $C_{15}=$ | 7 | 12 |
| $C_{18}=$ | 2 | 5 |
| $C_{21}=$ | 1 | 3 |

The present process shows unique advantages for the use of ultra large pore MCM-41 catalyst in olefin oligomerization reactions. Compared to ZSM-5 and ZSM-23 medium pore zeolites, the recently discovered mesoporous MCM-41 catalysts show higher activity and greater selectivity for the formation of trimers and tetramers for propylene oligomerization. The degree of branching can be controlled by varing process variables.

The ability of ultra large pore MCM-41 zeolites to selectively oligomerize olefins, especially propylene, at low temperature (i.e. <100° C.) to trimers and tetramers is unexpected and represents a significant improvement over previous catalysts. The high activity allows for control of branching index by varying the process parameters such as pressure and feed flowrate.

The disclosed catalyst for light olefin oligomerization provides the flexibility to adjust product selectivity and branching index. In contrast, ZSM-5 and ZSM-23 require a significantly higher operating temperature which results in the production of a broad range of hydrocarbons. The high activity of ultra-large pore MCM-41 allows for lower temperature operation which results in selective dimer, trimer and tetramer formation and may improve catalyst stability. For propylene oligomerization, MCM-41 provides unique selectivity toward $C_6$ and $C_9$ olefinic hydrocarbons.

A complete propylene conversion, increasing temperature results in higher MW product formation. Increasing pressure causes an increase in activity and a shift in selectivity to lower MW products as shown in Table D.

TABLE D

| Pressure | Temp (°C./°F.) | WHSV | Conv | \multicolumn{6}{c}{Olefin Selectivity} |
|---|---|---|---|---|---|---|---|---|---|

| Pressure | Temp (°C./°F.) | WHSV | Conv | $C_6$ | $C_9$ | $C_{12}$ | $C_{15}$ | $C_{18}$ | $C_{21}$ |
|---|---|---|---|---|---|---|---|---|---|
| 250 psig | 96/205 | 0.25 | 75% | 5 | 38 | 36 | 18 | 2 | 1 |
| 250 psig | 96/205 | 1.00 | 18% | 17 | 41 | 31 | 10 | 1 | 0 |
| 1000 psig | 96/205 | 1.00 | 85% | 8 | 60 | 25 | 6 | 1 | 0 |

The catalyst exhibits excellent short-term stability, showing no activity loss during a 29 days on stream at 96° C., 1000 psig and 1 WHSV.

TABLE E

| DOS | Conv | $C_6$ | $C_9$ | $C_{12}$ | $C_{15}$ | $C_{18}$ |
|---|---|---|---|---|---|---|
| 11 | 85% | 8 | 62 | 23 | 6 | 1 |
| 29 | 84% | 8 | 60 | 25 | 6 | 1 |

High pressures are employed to maximize olefin conversion, while low temperatures are desirable to minimize side reactions such as oligomer cracking, cyclization, and hydrogen transfer. The conversion of propane typically requires conditions far more severe than those necessary for propylene oligomerization. Due to the large difference in the boiling points of $C_3$ feed components and $C_6^+$ products, separation of these fractions may be easily accomplished. If the oligomerization reactor is operated at conditions which maximize propylene conversion, the $C_3$ stream obtained from the first separation unit will consist primarily of propane.

In the following Example F a propene-containing $C_3$ refinery stream is converted selectively employing MCM-41 Catalyst prepared according to Example 13. The reaction is conducted in an isothermal tubular reactor at about 120° C. (250° F.), 1500 psig and 1.8 WHSV, based on active catalyst.

TABLE F

Propylene Oligomerization over MCM-41
250° F., 1500 psig, 1.8 WHSV $C_3^=$

| | |
|---|---|
| Conversion, wt % | 87 |
| Selectivity, wt % | |
| $C_6$ Olefins | 11 |
| $C_9$ Olefins | 59 |
| $C_{12}$ Olefins | 20 |
| $C_{15}$ Olefins | 5 |
| $C_{18}^+$ Olefins | 5 |

As shown in Table F, the $C_6^+$ products consisted primarily of propylene trimers and tetramers. The reaction effluent from the primary stage oligomerization is readily separated by cooling, flashing and phase separation to recover a gaseous stream comprising mainly unconverted $C_3$ aliphatics and a condensed liquid stream consisting essentially of $C_6^+$ branched olefins. Sorption of heavier components from the $C_3$ stream can be effected by contact with a recyled liquid stream, for instance from second state separation. The normally liquid intermediates are separated from unconverted $C_3$ feedstock and cracked in a secondary stage reactor at high temperature and short contact time to produce significant amounts of propylene as well as $C_4$ and $C_5$ olefins. As shown in Table G below, the cracking experiments were conducted over MCM-22 at 900° F., 50 psig total pressure, 6 WHSV oligomer feed, and sufficient nitrogen to maintain hydrocarbon contact times near one second to yield a propylene-rich $C_3$ product stream. The tertiary olefins are produced in particularly high yield, especially when compared to their corresponding carbon number linear olefins. Isobutylene is found to be present in greater than equilibrium amounts at reaction temperature (e.g.—greater than 1:1).

This process may also be employed for paraffin/olefin separation of streams containing $C_4$ and $C_5$ fractions. Disproportionation of the oligomers is described below.

Description of Preferred Zeolite Cracking Catalysts

Careful selection of catalyst components to optimize $C_3$–$C_4$ and isoalkene selectivity is important to overall success of the process. The catalyst may consist essentially of MCM-22 aluminosilicate zeolite, having an acid cracking activity less than 15 (standard alpha value) and moderately low constraint index (C.I. = 1.5). The moderately constrained medium pore zeolite has a pore size of about 5–8 Å, able to accept oligomeric components found in the primary stage effluent.

Zeolite hydrocarbon upgrading catalysts preferred for use herein include the medium pore shape-selective crystalline aluminosilicate zeolites having the structure of MCM-22 and having acid cracking activity (alpha value) of about 1–15 based on active catalyst weight. While active catalyst consisting essentially of MCM-22 is preferred, it may be advantageous to employ this in combination with other catalytic materials, such as the medium pore zeolites. Representative of the ZSM-5 type medium pore shape selective zeolites are ZSM-5, ZSM-11, ZSM-12, ZSM-22, ZSM-23, ZSM-35, ZSM- 48, Zeolite Beta, SSZ-25 (U.S. Pat. No. 4,954,325), PSH-3 (U.S. Pat. No. 4,439,409) and mixtures thereof with similarly structured catalytic materials. Mixtures of MCM-22 with medium (i.e., about 5-7 Å) or larger pore zeolites, such as Y, mordenite, or others having a pore size greater than 7 Å) may be desirable. MCM-41 may may be employed in both the primary oligomerization stage reactor and secondary stage cracking reactor; however, greater selectivity for the desired lower olefins is realized using shape selective catalyst, preferably MCM-22 or the like, in the second stage.

MCM-22 synthesis is disclosed in U.S. Pat. No. 4,954,325 (M. Rubin L and P. Chu) and in olefin conversion in U.S. Pat. No. 4,956,514 (C. T. W. Chu), incorporated by reference. While suitable zeolites having a coordinated metal oxide to silica molar ratio of 20:1 to 500:1 or higher may be used, it is advantageous to employ standard MCM-22, suitably modified if desired to adjust acidity. A typical zeolite catalyst component having Bronsted acid sites may consist essentially of aluminosilicate zeolite with 5 to 95 wt. % silica and/or alumina binder, and having an acid cracking activity (alpha value) less than 15.

In selective olefin cracking or disproportionation reactions, it is advantageous to employ a standard zeolite having a silica:alumina molar ratio of 25:1 or greater in a once-through fluidized bed unit to convert about [5 to 70 weight percent, preferably about 10 to 50 wt. %], of the C6–C18 intermediate hydrocarbons in a single pass.

The olefin cracking or disproportionation process step of the present invention can be suitably carried out by contacting the olefinic feed with zeolite MCM-22 catalyst under moderate olefin conversion conditions, e.g., a temperature of from about 250° to about 700° C., preferably from about 300° to about 450° C., a pressure of from 100 to about 1500 kpa, preferably from about 150 to about 500 kpa and an WHSV of from about 0.1 to about 100 hr$^{-1}$, preferably from about 0.2 to about 20 hr$^{-1}$.

A significant advantage of MCM-22 catalyst is the high proportion of tertiary $C_4$-$C_5$ olefins. For instance, the ratio of isobutene: n-butene is typically greater than equilibrium.

Example G—Selective C6+ olefin conversion reactions are demonstrated to show selectivity in producing lower olefins and isoalkenes. This example of olefin cracking is conducted in a fixed bed reactor using steamed MCM-22 catalyst. In the reactor, catalyst is heated to 425° C. (900° F.) under nitrogen and maintained at this temperature and 450 kPa (50 psig) at weight hourly space velocity of 6/hr. The results from studies of intermediate oligomer cracking over MCM-22 are displayed in Table G To demonstrate the second stage reaction, highly branched oligomers formed over MCM-41 in the primary reaction stage are recovered from primary stage effluent and converted to lower olefins rich in propylene, butene isomers, amylenes and other olefins over MCM-22. The feedstream for the secondary stage reaction consists essentially of the $C_6$–$C_{18}$ oligomers of propene, predominantly dimer, trimer and tetramer. However, it may be economically advantageous to pass the entire primary stage effluent, including unreacted propene in cascade flow through the staged reactors.

TABLE G

| Oligomer Cracking over MCM-22 900° F., 50 psig, 6 WHSV $C_9^=$, 2000 GHSV Nitrogen | |
|---|---|
| Reactor Effluent, wt % | |
| Total $C_1$-$C_2$ | 0.7 |
| Propylene | 16.0 |
| Propane | 0.3 |
| Isobutylene | 14.8 |
| Linear Butenes | 14.7 |
| Isoamylenes | 19.5 |
| Linear Pentenes | 8.6 |
| $C_4$-$C_5$ Paraffins | 2.2 |
| $C_6$ Olefins | 10.2 |
| $C_6$ Paraffins + Cyclics | 1.2 |
| Total $C_7^+$ | 11.6 |

As shown in Table G, the cracking of the $C_6^+$ olefins yielded 16.0 wt. % propylene and only 0.3 wt. % propane, thus providing the highly-olefinic $C_3$ stream. The other products derived from this reaction were primarily $C_4^+$ olefins, which may be recycled to the cracking reactor to enhance propylene yield. However, olefins in the effluent stream may also be employed for the production of clean fuels.

The secondary stage reaction effluent may be separated conventionally by distillation or the like to recover an olefinic product stream rich in propene and $C_4$-$C_5$ tertiary olefins, which may be converted to MTBE and/or TAME; and wherein a $C_6^+$ heavy hydrocarbon may be recovered to recycle for further conversion and/or interstage separation. It is feasible to recover propene and butenes as an enriched olefin product stream, with a $C_5^+$ stream rich in tertiary olefins being partially etherified as a gasoline blending component.

In addition to the above reaction run, the selective cracking or disproportionation of $C_6^+$ intermediate olefins may potentially be performed in many other reactor configurations; however, fluidized bed configuration is preferred, particularly at high temperature (300°-550° C.) and short-contact time (<10 sec) conditions. Moving-bed and fixed-bed reactors are also viable for high activity and stable catalysts which might not require frequent regeneration. Preferred process conditions for fixed and moving -bed configuration would be in lower reactor temperature, space velocities (1-10 WHSV).

Example H—Using low pressure/short contact time conditions, MCM-22 catalyst was preconditioned with decene feedstock at 800° F., 50 psig, and 6 WHSV for 72 hours to reach steady state condition. Thereafter the $C_6$-$C_{18}$ oligomer feedstream from the primary stage effluent was reacted at 69% conversion. As seen in Table H, the product stream contained high yields of $C_3$-$C_5$ olefins and low amounts of paraffins.

TABLE H

| Propylene Oligomer Cracking over MCM-22 (800° F., 50 psig, 5.9 WHSV) | |
|---|---|
| Conv. to $C_5^-$ (wt %) | 69 |
| $C_5^-$ Product Dist., wt % | |
| Total $C_1$-$C_2$ | 0.4 |
| Propylene | 16.8 |
| Isobutylene | 22.3 |
| Linear Butenes | 17.4 |
| Isoamylenes | 28.7 |
| Linear Pentenes | 11.0 |
| $C_3$-$C_5$ Paraffins | 3.4 |

Among the $C_4$ olefins, the ratio of isobutylene to linear butenes (1.28) exceeded the equilibrium value (0.97), while branched/linear ratio for the $C_5$ olefins (2.61) was lower than that expected at equilibrium (3.18). Within the $C_6^=$ eluting from the cracking reactor, high yields of branched hexenes were found, with only minor amounts of $C_6$ cyclic compounds formed during the two-stage conversion of propylene.

COMPARATIVE EXAMPLE I

Combining the results from the first and second stages (F and H), the overall yield of branched $C_4$-$C_5$ olefins exceeded 30 wt. % with most of the other effluent hydrocarbons also being olefins. As seen in Table I, the isobutylene/isoamylene yield observed during this two-stage propylene conversion experiment is significantly higher than that reported for the one-stage process (30.6 vs. 19.8 wt. %).

TABLE I

Comparison of Two-Stage Propylene Conversion With Typical Single Stage Olefin Interconversion

|  | Two-Stage* | One-Stage** |
|---|---|---|
| Overall $C_3^=$ Conv. | 76.9 | 56.1 |
| Product Yields, wt % |  |  |
| Propylene | 23.1 | 43.9 |
| Isobutylene | 13.4 | 10.7 |
| Linear Butenes | 10.4 | 9.1 |
| Isoamylenes | 17.2 | 9.1 |
| Linear Pentenes | 6.6 | 3.6 |
| Total $iC_4^=$, $iC_5^=$ | 30.6 | 19.8 |
| Total $C_1$-$C_2$ | 0.2 | 0.4 |
| $C_3$-$C_5$ Paraffins | 2.0 | 3.1 |
| Total $C_6$ | 27.1 | 20.2 |

*First Stage: MCM-41, 250° F., 1500 psig, 1.8 WHSV
Second Stage: MCM-22, 800° F., 50 psig, 5.9 WHSV
**Conditions: ZSM-5, 667° F., 25 psia, 10.0 WHSV Represents conditions of highest iso-olefin yield

We claim:

1. A multistage process for upgrading a mixed $C_3$-$C_5$ aliphatic feedstock containing lower alkene component by oligomerizing the lower alkene component by contacting the feedstock in a primary stage with acid porous solid catalyst under selective oligomerization conditions to produce highly branched heavier oligomeric intermediate hydrocarbons in the substantial absence of product lower in molecular weight than dimer material; the primary stage catalyst comprising an inorganic, porous crystalline phase material having, after calcination, a hexagonal arrangement of uniformly-sized pores having diameters of at least about 13 Angstrom Units and exhibiting a hexagonal electron diffraction pattern that can be indexed with a $d_{100}$ value greater than about 18 Angstrom Units; and catalytically reacting primary stage effluent containing branched oligomeric hydrocarbons under olefin disproportionation conditions effective to produce $C_4$-$C_5$ tertiary olefin product.

2. The process of claim 1 wherein said crystalline phase has an X-ray diffraction pattern following calcination with at least one peak whose d-spacing corresponds to the $d_{100}$ value from the electron diffraction pattern.

3. The process of claim 1 wherein said crystalline phase exhibits a benzene adsorption capacity of greater than about 15 grams benzene per 100 grams at 50 torr and 25° C.

4. The process of claim 1 wherein said crystalline phase has a composition expressed as follows:

$$M_{n/q}(W_aX_bY_cZ_dO_h)$$

wherein M is one or more ions; n is the charge of the composition excluding M expressed as oxides; q is the weighted molar average valence of M; n/q is the number of moles or mole fraction of M; W is one or more divalent elements; X is one or more trivalent elements; Y is one or more tetravalent elements; Z is one or more pentavalent elements; a, b, c, and d are mole fractions of W, X, Y, and Z, respectively; h is a number of from 1 to 2.5; and $(a+b+c+d)=1$.

5. The process of claim 4 wherein the sum $(a+b+c)$ is greater than d, and $h=2$.

6. The process of claim 4 wherein W is a divalent first row transition metal or magnesium; X is selected from the group consisting of aluminum, boron, gallium and iron; Y is silicon germanium; and Z comprises phosphorus.

7. The process of claim 4 wherein W comprises cobalt, X comprises aluminum, Y comprises silicon and Z comprises phosphorus.

8. The process of claim 5 wherein W from a divalent first row transition metal or magnesium; X is selected from the group consisting of aluminum, boron, gallium and iron; Y is selected from silicon or germanium; and Z comprises phosphorus.

9. The process of claim 5 wherein W comprises cobalt, X comprises aluminum, Y comprises silicon and Z comprises phosphorus.

10. The process of claim 4 wherein a and d are 0 and $h=2$; and wherein X is selected from the group consisting of aluminum, boron, gallium and iron and Y is selected from silicon or germanium.

11. The process of claim 4 herein X comprises aluminum and Y comprises silicon.

12. The process of claim 4 wherein original ions are replaced, at least in part, with an ion or a mixture of ions selected from the group consisting of hydrogen and hydrogen precursors, rare earth metals, and metals of Groups IA, IIA, VIIA, VIIIA, IB, IIB, IIIB, IVB and VIIB of the Periodic Table of the Elements.

13. The process of claim 12 wherein the crystalline material results from thermal treatment.

14. The process of claim 12 wherein said replacing ions comprise hydrogen or a hydrogen precursor.

15. The process of claim 1 wherein said catalyst comprises a matrix.

16. The process of claim 15 wherein said matrix comprises alumina, silica, clay or mixtures thereof.

17. The process of claim 1 including the step of selectively cracking the separated heavier alkene oligomer product of oligomerization in a secondary process stage in contact with a medium pore metallosilicate cracking catalyst at elevated temperature to produce lower alkene rich in $C_3$-$C_5$ alkene.

18. The process of claim 17 wherein the oligomerization reaction yields a major amount of dimer and trimer, wherein said cracking catalyst comprises MCM-22 zeolite, and wherein the secondary stage cracking reaction produces a major amount of $C_3$-$C_5$ alkenes rich in isoalkenes.

19. A two-stage process for upgrading $C_3$-$C_5$ lower alkene feedstock to produce tertiary alkene comprising the steps of:

a) oligomerizing the lower alkene in a first reaction stage by contacting said feedstock under catalytic conversion conditions with acid metallosilicate solid catalyst having the structure of MCM-41 with hexagonal honeycomb lattice structure consisting essentially of uniform pores in the range of about 20 to 100 Angstroms, thereby producing $C_{6}+$ intermediate hydrocarbons rich in isoalkenes; and b) further converting the intermediate hydrocarbons from the first reaction stage at elevated temperature in the presence of zeolite disproportionation catalyst to produce $C_4$-$C_5$ tertiary alkenes.

20. The process of claim 19 wherein said metallosilicate comprises tetrahedrally coordinated Al, Ga or F atoms; wherein oligomerization reaction temperature is about 40° to 250° C.; pressure is about 100–13,000 pKa range; and weight hourly space velocity, based on active catalyst is about 0.1–5/hr WHSV.

21. The process of claim 19 wherein the feedstock consists essentially of propene, wherein the oligomerization reaction temperature is about 80° to 200°; and propene pressure is maintained above about 5000 kPa to obtain increased selectivity to hexene and nonene isomers.

22. The process of claim 20 wherein first reaction stage effluent is passed as a cascade feedstream, substantially unfractionated, to the second reaction stage.

23. A multi-stage process for catalytic upgrading of lower olefin to tertiary olefin which comprises:
contacting lower olefin feedstock under catalytic olefin oligomerization conditions with inorganic, porous, non-layered crystalline phase oligomerization catalyst material exhibiting, after calcination, an X-ray diffraction pattern with at least one peak at a d-spacing greater than about 18 Angstrom units and having a benzene adsorption capacity greater than 15 grams of benzene per 100 grams of said material at 50 torr and 25° C.; said oligomerization catalyst material having active Bronsted acid sites to produce heavier intermediate highly branched olefins, and selectively cracking said intermediate branched olefins at elevated temperature in contact medium pore zeolite cracking catalyst to produce isobutylene or isoamylene.

24. The process of claim 23 wherein said oligomerization catalyst material has a hexagonal arrangement of uniformly-spaced pores with at least 13 Angstroms diameter, and having a hexagonal electron diffraction pattern that can be indexed with a d100 value greater than 18 Angstrom units; and wherein said olefin comprises at least one $C_3$-$C_6$ alkene; and wherein said catalyst consists essentially of metallosilicate comprising tetrahedrally coordinated Al, Ga or F atoms.

25. The process of claim 23 wherein said oligomerization catalyst material consists essentially aluminosilicate having the structure of MCM-41; wherein oligomerization reaction temperature is about 40° to 250° C.; pressure is about 100–13,000 pKa range; and weight hourly space velocity, based on active catalyst is about 0.1–5/hr WHSV; wherein said cracking catalyst comprises MCM-22 zeolite; and wherein the cracking reaction produces a major amount of $C_3$-$C_5$ cracked olefins rich in iso-olefin.

26. The process of claim 23 wherein said oligomerization catalyst material consists essentially a metallosilicate having hexagonal honeycomb lattice structure consisting essentially of uniform pores in the range of about 20 to 100 Angstroms.

27. A process for catalytic upgrading of lower olefin which comprises:

a) contacting lower olefin feedstock under catalytic oligomerization reaction conditions at moderate temperature with acid metallosilicate solid catalyst having the structure of MCM-41 with hexagonal honeycomb lattice structure consisting essentially of uniform pores in the range of about 20 to 100 Angstroms, thereby producing $C_{6}+$ intermediate hydrocarbons rich in isoalkenes; and b) further converting the intermediate hydrocarbons from the first reaction stage at elevated temperature in the presence of zeolite disproportionation catalyst to produce $C_4$-$C_5$ tertiary alkenes.

28. The process of claim 27 wherein said oligomerization reaction is conducted at temperature of about 40° to 250° C. for at least 80% conversion of lower olefins at pressure of about 100–13,000 pKa range and moderate space velocity under selective oligomerization conditions to produce highly branched heavier oligomer in the substantial absence of product lower in molecular weight than dimer material;
selectively cracking at least a portion of the heavier oligomer product of oligomerization in a secondary process stage in contact with a medium pore metallosilicate cracking catalyst at elevated temperature to produce lower alkene rich in $C_3$-$C_5$ alkene.

29. The process of claim 28 wherein the oligomerization reaction yields a major amount of dimer and trimer, wherein said cracking catalyst comprises MCM-22 zeolite, and wherein the secondary stage cracking reaction produces a major amount of $C_3$-$C_5$ cracked Olefins rich in iso-olefin.

30. The process of claim 29 wherein isobutene is produced in amount greater than at equilibrium with corresponding linear butenes.

31. In the process of olefin interconversion wherein a lower olefin feedstock is converted catalytically to a mixture of linear olefins and iso-olefins, the improvement which comprises two stages of catalysis including the sequential steps of:
oligomerizing the lower olefin feedstock in a first catalytic stage under low severity oligomerization conditions in contact with a selective acid mesoporous oligomerization catalyst intermediate to produce intermediate predominantly highly branched dimeric, trimeric and tetrameric olefins; and
disproportionating at least a portion of intermediate olefins in a separate second catalytic stage under selective olefin cracking conditions in contact with a medium pore acid catalyst to provide enhanced yield of tertiary olefins.

32. The process of claim 31 wherein $C_4$-$C_5$ iso-olefins are produced in a ratio to linear $C_4$-$C_5$ olefins greater than 1:1.

* * * * *

UNITED STATES PATENT AND TRADEMARK OFFICE
CERTIFICATE OF CORRECTION

PATENT NO. : 5,134,241
DATED : July 28, 1992
INVENTOR(S) : Le et al.

It is certified that error appears in the above-identified patent and that said Letters Patent is hereby corrected as shown below:

Abstract, 4th from last line, "pKa" should be --kPa--.

Abstract, last line, "isoalkenese" should be --isoalkenes--.

Column 32, line 17, "silicon germanium" should be --silicon or germanium--.

Column 32, line 22, "from" should be --is a--.

Column 33, line 12, "pKa" should be --kPa--.

Column 33, line 54, "pKa" should be --kPa--.

Column 34, line 21, "pKa" should be --kPa--.

Signed and Sealed this

Ninth Day of November, 1993

Attest:

BRUCE LEHMAN

Attesting Officer

Commissioner of Patents and Trademarks